United States Patent [19]

Sipido

[11] 4,262,004
[45] Apr. 14, 1981

[54] 2,3-DIHYDRO-IMIDAZO[2,1-B]BENZO-THIAZOLE COMPOSITIONS TO TREAT DEPRESSIONS

[75] Inventor: Victor Sipido, Merksem, Belgium
[73] Assignee: Janssen Pharmaceutica, N.V., Beerse, Belgium
[21] Appl. No.: 50,734
[22] Filed: Jun. 21, 1979
[51] Int. Cl.$^3$ ............................................ C07D 277/60
[52] U.S. Cl. ..................................... 424/270; 548/151
[58] Field of Search ......................... 548/151; 424/270

[56] References Cited

U.S. PATENT DOCUMENTS

| | | | |
|---|---|---|---|
| 3,974,286 | 8/1976 | Paget ..................................... | 424/270 |
| 4,042,583 | 8/1977 | Acheson et al. ..................... | 424/270 |
| 4,104,500 | 8/1978 | Weisenborn et al. ................ | 424/270 |

OTHER PUBLICATIONS

CA 82, p. 509, 31326h (1975), Abstracting Russian Patent 436,058.
Ogura et al., Chem. Pharm. Bull., 18(10), 1981–1986 (1970).
Parrick et al., Chem. and Ind., 1970, 39, 1261–1262.

Primary Examiner—Nicholas S. Rizzo
Attorney, Agent, or Firm—Geoffrey G. Dellenbaugh

[57] ABSTRACT

This invention relates to a novel series of 2,3-dihydro-imidazo[2,1-b]benzothiazoles which display monoamine oxidase inhibiting activities.

3 Claims, No Drawings

2,3-DIHYDRO-IMIDAZO[2,1-B]BENZOTHIAZOLE COMPOSITIONS TO TREAT DEPRESSIONS

BACKGROUND OF THE INVENTION

In Russian Pat. No. 443,039, in Chem. Pharm. Bull. 18 (10) 1981-1986 (1970) and in Chem. Ind. 1970, (39), 1261-2 there are described a number of imidazo[2,1-b]benzothiazole derivatives, which are useful as pharmaceuticals. The compounds of the present invention differ from these prior art compounds by the saturation of the double bond between $C_2$ and $C_3$ and by their monoamine oxidase inhibitor activities, resulting in their usefulness as antidepressants and as anti-Parkinsonism agents.

DESCRIPTION OF THE PREFERRED EMBODIMENTS

This invention is concerned with novel 2,3-dihydro-imidazo[2,1-b]benzothiazoles, which may structurally be represented by the formula

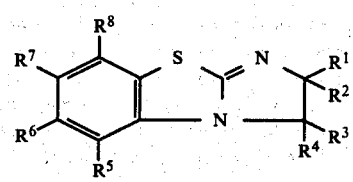

(I-a)

and the pharmaceutically acceptable acid addition salts thereof, the imidazo[2,1-b]benzothiazolium salts of formula

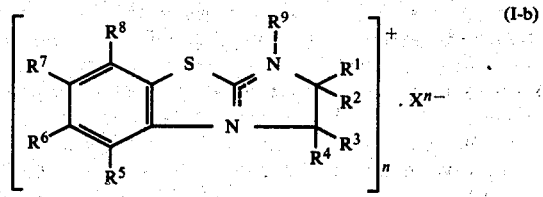

(I-b)

and metal salt complexes thereof, wherein:

$R^1$ and $R^3$ are each independently selected from the group consisting of hydrogen and lower alkyl;

$R^2$ and $R^4$ are each independently selected from the group consisting of hydrogen, lower alkyl, aryl, aryl-lower alkyl, lower alkyloxy-lower alkyl or aryloxy-lower alkyl.

$R^5$, $R^6$, $R^7$ and $R^8$ are each independently selected from the group consisting of hydrogen; halo; nitro; alkyl having from 1 to 20 carbon atoms; cycloalkyl having from 3 to 6 carbon atoms; hydroxy; lower alkyloxy; aryloxy; α-hydroxy-arylmethyl; amino; mono- and dialkyl-amino; mono-, di- and trihalo-lower alkylamino; lower alkenylamino; lower alkynylamino; (aryl-lower alkyl)amino; (lower alkyloxy-lower alkyl)amino; (hydroxylower alkyl)amino; (aryloxy-lower alkyl)amino; [mono- and di(lower alkyl)aminolower alkyl]amino; lower alkanoylamino; N-(lower alkyl)lower alkanoylamino; aminocarbonylamino; (1-lower alkyl-4-piperidinyl)amino; cycloalkylamino wherein said cycloalkyl represents a mono-, bi-, tri- or tetracyclic hydrocarbon radical having from 3 to 10 carbon atoms; and a radical of the formula

wherein $R^{10}$ is selected from the group consisting of hydrogen, lower alkyl, lower alkenyl and lower alkynyl; or, when taken together $R^5$ and $R^6$, $R^6$ and $R^7$, or $R^7$ and $R^8$ may form a tri- or tetramethylene bridge or complete a fused benzene nucleus;

$R^9$ is a member selected from the group consisting of lower alkyl, lower alkenyl, lower alkynyl and aryllower alkyl; and X is a pharmaceutically acceptable anion and n represents the valency of the anion;

wherein aryl as used in the foregoing definitions is phenyl, optionally substituted with 1 to 3 substituents each independently selected from the group consisting of halo, lower alkyl, lower alkyloxy and trifluoromethyl; and aroyl is arylcarbonyl.

As used in the foregoing and in the following definitions, the term "halo" is generic to fluoro, chloro, bromo and iodo; "lower alkyl" is meant to include straight and branched hydrocarbon radicals having from 1 to 6 carbon atoms such as, for example, methyl, ethyl, 1-methylethyl, 1,1-dimethylethyl, propyl, 1-methylpropyl, 2-methylpropyl, butyl, pentyl, hexyl and the like; "alkyl" is meant to include the above mentioned meaning of "lower alkyl" and the higher homologous having from 7 to 20 carbon atoms such as, for example, heptyl, octyl, nonyl, decyl, undecyl, dodecyl and the like; "lower alkenyl" and "lower alkynyl" are meant to include straight and branched alkenyl, respectively alkynyl, radicals having from 2 to 6 carbon atoms, such as, for example, ethenyl, 2-propenyl, 2-butenyl and the like, and, respectively, ethynyl, 2-propynyl, 2-butynyl and the like; "cycloalkyl, having from 3 to 6 carbon atoms", as used in the definition of $R^5$, $R^6$, $R^7$ and $R^8$ refers to cyclopropyl, cyclobutyl, cyclopentyl and cyclohexyl; and "cycloalkyl, having from 3 to 10 carbon atoms" as it is employed as part of cycloalkylamino in the definition of said $R^5$, $R^6$, $R^7$ and $R^8$, refers to mono-, bi-, tri- and tetracyclic hydrocarbon radicals such as, for example, cyclopentyl, cyclooctyl, bicyclo[3,2,1]octane, tricyclo[3,3,1,1$^{3,7}$]decane and the like.

The anion $X^{n-}$ in the foregoing formula (I-b) may be any pharmaceutically acceptable anion but is preferably an ion arizing from a reactive ester such as, for example, a halide ion, preferably a chloride-, bromide- or iodide ion, or another ion arizing from a reactive ester such as a methanesulfonate or a 4-methylphenylsulfonate ion. Other pharmaceutically acceptable anions falling within the scope of $X^{n-}$ are, for example, anions arizing from mineral acids, e.g., nitrate, sulfate and phosphate anions, and anions arizing from pharmaceutically acceptable organic acids such as, for example, the anions of acetic-, propanoic- and the like acids.

The compounds of formula (I-a) can be derived from an appropriately substituted 2-(2-benzothiazolylamino)ethanol of formula (II) or from an appropriate 2-imino-3(2H)-benzothiazoleethanol of formula (III) by cyclizing said intermediates following art-known cyclizing procedures.

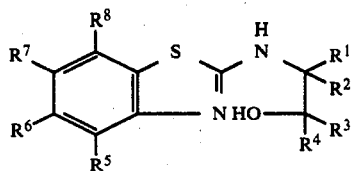

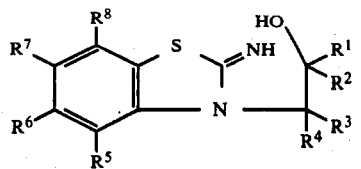

$R^1$, $R^2$, $R^3$, $R^4$, $R^5$, $R^6$, $R^7$ and $R^8$ are as previously described.

The above-mentioned cyclization-reactions may be carried out by stirring and heating the intermediates of formula (II) or (III) in an aqueous strong acidic medium such as, for example, aqueous hydrochloric acid, aqueous sulfuric acid and the like, if desired in admixture with a reaction-inert organic solvent such as 1,4-dioxane, tetrahydrofuran and the like.

In order to improve the yields of said cyclization-reactions the hydroxyl function of the intermediates (II) or (III) may be previously converted into a reactive ester residue such as, for example, halo, preferably chloro, bromo or iodo, or a sulfonyloxy group, e.g., methylsulfonyloxy, 4-methylphenylsulfonyloxy and the like; by reacting said alcohols (II) or (III) with an appropriate halogenating agent, e.g., thionyl chloride, phosphorpentabromide and the like, or with an appropriate sulfonating agent, e.g., methylsulfonyl chloride, 4-methylphenylsulfonyl chloride and the like. The thus obtained intermediates are then cyclized by stirring the latter in an appropriate solvent such as, for example, an amide, e.g., N,N-dimethylformamide and the like; dimethylsulfoxide and the like. Somewhat elevated temperatures and the addition of a suitable base such as, for example, an alkali metal or an earth alkaline metal carbonate or hydrogen carbonate, e.g., sodium hydrogen carbonate, potassium carbonate and the like, may advantageously be used to enhance the rate of the reaction.

The compounds of formula (I-a) may also be prepared by cyclizing an appropriately substituted 1-aryl-4,5-dihydro-2-mercapto-1H-imidazole of formula (IV), wherein L represents an appropriate leaving group such as, for example, halo, preferably chloro, bromo or iodo.

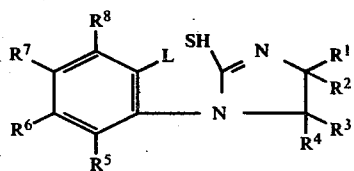

$R^1$, $R^2$, $R^3$, $R^4$, $R^5$, $R^6$, $R^7$ and $R^8$ are as previously described.

Said cyclization-reaction may be carried out following art-known cyclizing procedures generally known in the art, e.g., by stirring and heating the intermediate (IV) in the presence of a suitable reaction-inert solvent, e.g., N,N-dimethylformamide and the like, if desired in the presence of an appropriate base, e.g., sodium carbonate and the like.

Certain compounds of formula (I-a) may be derived from other appropriately substituted compounds (I-a) by introducing or modifying certain substituent groups according to generally known methods of effecting transformations of functional groups.

Specific examples of functional group transformations which can easily be carried out are as follows:

(i) Nitro-substituted compounds may be prepared by nitrating the corresponding unsubstituted analogs in the usual manner, e.g., by stirring and heating a nitrate salt of the latter in an appropriate strong acidic medium, e.g., iqueous sulfuric acid and the like.

(ii) Nitro-substituted compounds can be converted into the corresponding primary amines according to standard nitro-to-amine reducing procedures, e.g., by catalytically hydrogenating the nitro compound in the presence of an appropriate catalyst, e.g., Raney-nickel, palladium-on-charcoal or platinum-on-charcoal.

(iii) Primary amines can in turn be alkylated to produce secondary and tertiary amines following standard N-alkylation procedures. For example, said N-alkylation may be performed by the reaction of the amine with an appropriate reactive ester, e.g. a halide, a methanesulfonate or a 4-methylphenylsulfonate. Otherwise there may be carried out a reductive amination by subjecting a mixture of the amine with an appropriate carbonyl compound in the presence of an appropriate catalyst, e.g. platinum-on-charcoal to a catalytic hydrogenation.

Similarly such a reductive amination may also be achieved by reducing a mixture of the amine and an appropriate carboxylic acid with an appropriate reducing agent, e.g., sodium borohydride. In order to prepare secondary amines it may be appropriate to first introduce an appropriate protecting group, thereafter introducing the desired substituent, and finally removing the protecting group. An example of an appropriate protecting group is a di-(lower alkyl) 2-methylenepropane dioate radical which may easily be introduced by the reaction of the amine with a di(lower alkyl) 2-(lower alkyloxymethylene)propanedioate, and which may easily be removed by acid hydrolysis, e.g. in aqueous hydrochloric acid.

(iv) Alkanoylamino-substituted compounds can be prepared by acylating the corresponding amine in the usual manner with an appropriate acylating agent, e.g. an acyl halide or acid anhydride. In order to prepare formylamino-substituted compounds their may be used formaldehyde and also N,N-dimethylformamide as an acylating agent.

(v) Compounds bearing an aminocarbonylamino substituent can be prepared by reacting the corresponding amine with an appropriate alkali or earth alkaline metal cyanate, e.g. potassium cyanate and the like.

(vi) Hydroxy-substituted compounds may be derived from the corresponding lower alkyloxy- or aryllower alkyloxy-substituted compounds by treating the latter with a strong non-oxidizing acid, e.g. hydrobromic acid in acetic acid.

(vii) Compounds bearing an α-hydroxy-arylmethyl substituent can be derived from the corresponding aroyl-substituted analogs by reducing the carbonyl group of the latter using an appropriate reducing agent, such as, sodium borohydride and the like.

The compounds of formula (I-a) may conveniently be converted into their quaternary ammonium salts of formula (I-b) by reacting a compound of formula (I-a) with a reagent of formula (V), wherein $R^9$ is as previously defined and Z is a reactive ester group such as, for example, halo, e.g., chloro, bromo or iodo, or a sulfonyloxy group, e.g., methylsulfonyloxy, 4-methylphenylsulfonyloxy and the like, and, if desired, subsequently exchanging the anion Z of the thus obtained compound of formula (I-c) for another therapeutically acceptable anion X, having n as valency.

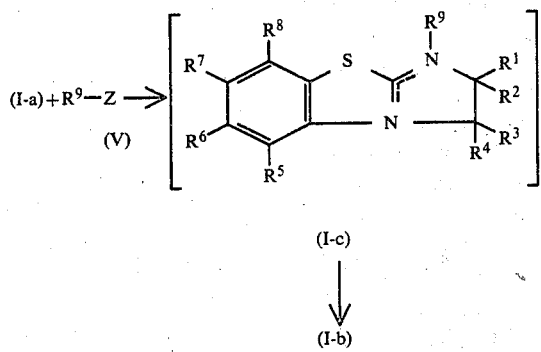

The reaction of (I-a) with (V) is conveniently carried out by stirring and heating the reactants together in the presence of a suitable reaction-inert solvent such as, for example, a nitrile, e.g., acetonitrile, benzonitrile and the like; halogenated hydrocarbons, e.g., dichloromethane; and other common solvents including dimethylformamide and the like. Most preferably, the reaction is carried out at the reflux temperature of the reaction mixture.

The anion-exchange reaction may be accomplished following art-known methods such as, for example, by treating a compound of formula (I-c) with a large molar excess of an acid corresponding to the anion of the desired salt, or, more preferably, by bringing the salt of formula (I-c) into contact with an ion-exchange resin, which is saturated with the desired anion, and subsequently eluting the desired salt (I-b) from the resin with a suitable relatively polar solvent, or by first converting the salt (I-c) into the corresponding hydroxide and subsequently reacting the latter with an acid corresponding to the anion of the desired salt. The salt (I-c) can be converted into the corresponding hydroxide, e.g., by its reaction with a base or by contacting said salt with an ion-exchange resin, which is saturated with hydroxide ions, and eluting the thus obtained hydroxide from the ion-exchange resin with a suitable relatively polar solvent.

Metal salt complexes of compounds of formula (I-a) may be obtained by the complexation of the latter with an organic or inorganic transition metal salt, such as, for example, halides, nitrates, sulfates, phosphates, (Z)-butenedioates and the like of copper, manganese, zinc, iron and the like transition metals, wherein said transition metals may have any of their naturally existing valencies.

In practice, stoechiometrically defined metal salt complexes may be prepared by dissolving a compound of formula (I-a) in a water-miscible solvent such as, for example, warm ethanol, methanol, 1,4-dioxane or N,N-dimethylformamide, and adding thereto an aqueous solution of the desired metal salts such as, for example, $CuSO_4.5H_2O$, $Mn(NO_3)_2.4H_2O$, $FeCl_3.6H_2O$ and the like.

A number of the intermediates used in the foregoing preparations are known compounds, others may be prepared according to art-known methodologies of preparing similar compounds and some of them are novel and consequently their preparation will be described hereafter.

The intermediates of formula (II) may be prepared by cyclizing an appropriately substituted thiourea (VI) wherein the R-substituents are as previously defined and Y represents hydrogen or a reactive leaving group such as, for example, halo, e.g., chloro, bromo, iodo, following art-known procedures.

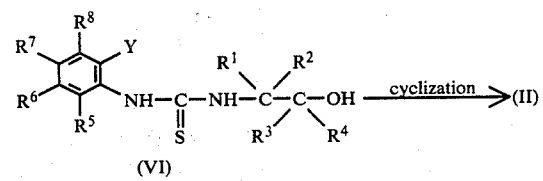

In case Y is a reactive leaving group the cyclization-reaction can be carried out by stirring and heating the thiourea (VI) in a suitable reaction-inert organic solvent, e.g., N,N-dimethylformamide and the like, preferably, in the presence of an appropriate base, such as an alkali metal or an earth alkaline metal carbonate or hydrogen carbonate or an alkali metal hydride, e.g., sodium carbonate, sodium hydride and the like. In case Y is hydrogen said cyclization may be carried out by stirring and heating the thiourea (VI) in a suitable reaction-inert solvent, e.g., trichloromethane, glacial acetic acid and the like, in the presence of a suitable halogenating agent, e.g., bromine and the like. The latter procedure may yield directly the corresponding compound of formula (I) when at least one of $R^3$ and $R^4$ is a sufficiently electronegative group such as, for example, an aryl group.

The intermediates of formula (VI), used as starting materials herein, can be prepared by reacting an appropriate arylisothiocyanate (VII) with an appropriately substituted 2-aminoethanol (VIII). In the following reaction equation all R-substituents have their previously defined meanings.

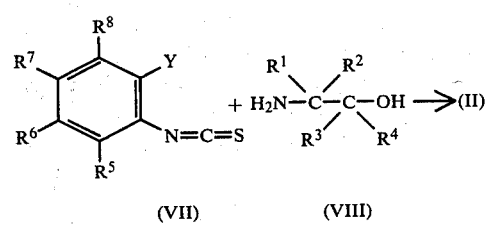

Said reaction is carried out by stirring and, if desired, heating the reactants together in the presence of a suitable reaction-inert solvent such as, for example, a lower alkanol, e.g., ethanol, 2-propanol and the like.

The isothiocyanates (VII), used as starting materials herein can be prepared following art-known methods of preparing such or similar products.

The intermediates of formula (III) can be prepared by N-alkylating an appropriately substituted 2-aminobenzothiazole (IX) with an appropriate alcohol (X) following art-known N-alkylating procedures, i.e., by stirring and, if desired, heating the reactants together in the presence of a suitable reaction-inert solvent such as, for example, a nitrile, e.g., acetonitrile and the like. In the following reaction equation the R-substituents are as previously defined and W represents a reactive ester residue such as, for example, halo, preferably, chloro, bromo or iodo, or a sulfonyloxy group, e.g., methylsulfonyloxy, 4-methylphenylsulfonyloxy and the like.

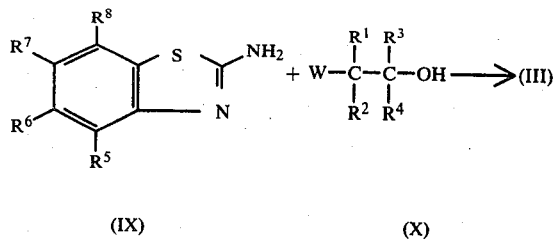

(IX)    (X)

The intermediates of formula (III) wherein $R^3$ is aryl, (III-a), are preferably prepared by the reaction of (IX) with an appropriate carbonyl compound of the formula (XI) yielding an intermediate of formula (XII), and subsequently reducing the latter with an appropriate reducing agent, e.g. sodium borohydride. The reaction of (IX) with (XI) may be carried out following the procedure described hereabove for the reaction of (IX) with (X).

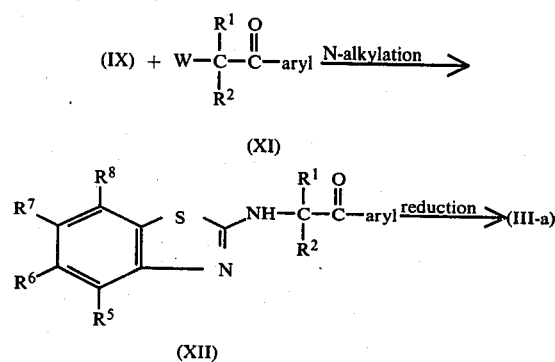

It is obvious that the compounds of formula (I) wherein $R^1$ is other than $R^2$ and/or $R^3$ is other than $R^4$ have at least one asymmetric carbon atoms and, consequently, said compounds may exist under different enantiomeric forms. Pure enantiomeric forms of the compounds (I) may be obtained by the application of art-known procedures such as, for example, separation of their diastereomeric salts with optically active acids and the like procedures. Isomers of compounds of formula (I) are naturally intended to be embraced within the scope of this invention.

The compounds of formula (I) have basic properties and thus may be converted to their therapeutically useful acid addition salts by reaction with an appropriate acid, for example, an inorganic acid such as hydrohalic acid, i.e., hydrochloric, hydrobromic or hydroiodic acid; sulfuric, nitric or thiocyanic acid; a phosphoric acid; and organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g. by reaction with alkali such as sodium or potassium hydroxide.

The compounds within the scope of this invention display valuable monoamine oxidase (M.A.O.) inhibiting properties. Monoamine oxidase has been classified into two types A and B which can be differentiated according to their substrate specificity and inhibitor sensitivity. In rat brain, for instance, tryptamine is oxidatively deaminated by the type A enzyme while β-phenylethylamine is preferentially catabolized by the type B enzyme.

The potencies of compounds of formula (I) as M.A.O.-inhibitors were determined in an in-vitro experiment as described below.

PREPARATION OF THE MONOAMINE OXIDASE EXTRACT

Male Wistar rats, weighing 150 to 200 g, are killed by decapitation. Brain and other tissues are quickly removed and homogenized in an ice cold 0.25 M sucrose solution with a homogenizer. The total homogenate is centrifuged at low speed (7000 g-min) in a refrigerated centrifuge. The supernatant is stored at 0° C. and the sediment, which contains cell nuclei, unbroken cells and debris, is rehomogenized in an ice cold 0.25 M sucrose solution and centrifuged again at 7000 g.min.. The thus obtained supernatants are combined to yield the monoamine oxidase extract.

DESCRIPTION OF THE IN-VITRO EXPERIMENTS

A mixture, containing 0.5 mmoles of [$^{14}$C]tryptamine (specific activity: 50.34 mCi/mmole) or 0.5 mmoles of [$^{14}$C] phenylethylamine hydrochloride (specific activity: 50.98 mCi/mmole), 113 mmoles of potassium phosphate (pH 7.4), the substance to test and 100 μl of the hereabove described monoamine oxidase extract in a total volume of 0.5 ml, is incubated at 37° C. for 20 minutes. The reaction is stopped by adding 0.2 ml of 2 N HCl and the reaction product is extracted in 6 ml of methylbenzene. 4 ml of the organic phase is counted for the radioactivity in a liquid scintillation spectrometer.

The data listed in tables 1 and 2 represent the concentrations of the tested compounds which inhibit 50% of the monoamine oxidase activity, using tryptamine, respectively β-phenylethylamine as substrate. The compounds listed in the tables are not given for the purpose of limiting the invention thereto but in order to exemplify the M.A.O. inhibitory activities of the compounds within the scope of formula (I).

TABLE I

| $R^a$ | $R^b$ | I.C.$_{50}$-value using as substrate in mole/liter: | |
|---|---|---|---|
| | | [$^{14}$C]tryptamine | [$^{14}$C]phenylethylamine . HCl |
| — | 7-OH | $2 \times 10^{-6}$ | — |
| — | 5-Cl | $1.2 \times 10^{-7}$ | $6 \times 10^{-7}$ |
| — | 7-OCH$_3$ | $2.8 \times 10^{-7}$ | $1.4 \times 10^{-5}$ |
| — | 7-OC$_6$H$_5$ | $4.5 \times 10^{-7}$ | $9.5 \times 10^{-8}$ |
| — | 6,7-(CH$_2$)$_3$ | $5.5 \times 10^{-8}$ | $1.2 \times 10^{-5}$ |
| — | 5,6-(CH=CH—CH=CH) | $6 \times 10^{-9}$ | $4 \times 10^{-6}$ |
| — | 7-c . C$_6$H$_{11}$ | $1.2 \times 10^{-8}$ | $6.5 \times 10^{-8}$ |
| — | 6-CO—C$_6$H$_5$ | $2.2 \times 10^{-7}$ | $3 \times 10^{-6}$ |
| 2-C$_6$H$_5$ | 7-C$_3$H$_7$ | $2.5 \times 10^{-6}$ | $6 \times 10^{-6}$ |
| — | 5-CH$_3$ | $2.2 \times 10^{-7}$ | $4 \times 10^{-6}$ |
| — | 6-C$_2$H$_5$ | $1.4 \times 10^{-7}$ | $10^{-5}$ |
| — | 7-C$_6$H$_{13}$ | $2 \times 10^{-8}$ | $4 \times 10^{-8}$ |
| — | 6-NH—C$_2$H$_5$ | $1.8 \times 10^{-8}$ | $4 \times 10^{-5}$ |
| — | 7-NH—C$_2$H$_5$ | $10^{-7}$ | $4.5 \times 10^{-5}$ |
| — | 8-NH—C$_2$H$_5$ | $2 \times 10^{-9}$ | $4 \times 10^{-5}$ |
| — | 6-NH—i . C$_3$H$_7$ | $1.8 \times 10^{-8}$ | $3.4 \times 10^{-5}$ |
| — | 7-NH—CH$_2$—C≡CH | $8 \times 10^{-7}$ | $5.5 \times 10^{-5}$ |
| — | 6-NH—CH(CH$_3$)—CH$_2$OH | $1.3 \times 10^{-7}$ | — |
| — | 6-NH—CH(C$_2$H$_5$)$_2$ | $6 \times 10^{-9}$ | $1.8 \times 10^{-6}$ |
| — | 6-NH—CH$_2$—(4-Cl—C$_6$H$_4$) | $2.6 \times 10^{-8}$ | $7 \times 10^{-8}$ |
| — | 7-NH—CH$_2$[3,4,5-(OCH$_3$)$_3$—C$_6$H$_2$] | $2 \times 10^{-5}$ | $7 \times 10^{-8}$ |
| — | 6-NH—CO—CH$_3$ | $1.8 \times 10^{-6}$ | $8.5 \times 10^{-5}$ |
| — | 6-NH—CO—NH$_2$ | $1.6 \times 10^{-6}$ | $1.2 \times 10^{-5}$ |
| — | 7-NH—CH=C(COOEt)$_2$ | $3.4 \times 10^{-6}$ | $3 \times 10^{-8}$ |
| — | 7-N(C$_3$H$_7$)—CH=C(COOEt)$_2$ | $2.2 \times 10^{-7}$ | $2.2 \times 10^{-6}$ |

TABLE 2

| Compound | I.C.$_{50}$-value using as substrate | |
|---|---|---|
| | [$^{14}$C]tryptamine in mole/liter | [$^{14}$C]phenylethylamine hydrochloride in mole/liter |
| (first compound: (CH$_3$)$_2$CH—NH substituted benzothiazoline, Cu$^{2+}$ 2 Cl$^-$) | $1 \times 10^{-9}$ | $4 \times 10^{-5}$ |
| (second compound: (COOEt)$_2$C=CH—N(C$_6$H$_{13}$) substituted, Br$^-$) | — | $1.8 \times 10^{-6}$ |

As can be seen from the data listed in tables 1 and 2, certain compounds within the scope of the present invention inhibit the enzyme activity at very low concentration when tryptamine is used as substrate, while a much higher concentration is required to elicit an inhibiting effect when a phenylethylamine substrate is used. Such compounds are preferably monoamine oxidase inhibitors of the type A. On the other hand certain compounds have better inhibiting properties when β-phenylethylamine is used as substrate and, obviously, such compounds have more monoamine oxidase properties of the type B.

As is generally known, compounds which are M.A.O.-inhibitors of the type A can be used as antidepressants while M.A.O.-inhibitors of the B-type can be used as anti-Parkinson agents. Since both types of activity are present in the subject compounds they can theoretically be used in both applications. However, it is obvious that compounds with prevailing M.A.O.-type A inhibiting activity are especially suited as antidepressants while those with prevailing M.A.O.-type B inhibiting properties are particularly useful as anti-Parkinson agents.

In view of the useful antidepressant and anti-Parkinson activity of the subject compounds of formula (I) this invention provides valuable pharmaceutical compositions comprising a compound of formula (I) or a pharmaceutically acceptable acid addition salt or a metal salt complex thereof in an amount which is effective to treat depression and/or Parkinsonism, as the active ingredient, in a solvent or a solid, semi-solid or liquid diluent or carrier. Further it provides an effective method of treating depression, respectively Parkinsonism by administering to the patient an amount of a compound of formula (I) which is effective in the relevant circumstances. Obviously, the compounds of formula (I) may optionally be used in combination with other therapeutically active substances. Pharmaceutical compositions comprising a compound of formula (I) as the active ingredient may be readily prepared according to conventional pharmaceutical techniques for the usual routes of administration.

Preferred compositions are in unit dosage form, comprising per dosage unit an effective quantity of the active ingredient in admixture with suitable carriers. Although the amount of the active ingredient per unit dosage may vary within rather wide limits, dosage units comprising from about 1 mg to about 500 mg and more particularly from about 5 mg to about 200 mg of the active ingredient are preferred.

The following examples are intended to illustrate and not to limit the scope of the present invention.

PREPARATION OF INTERMEDIATES

Example I

To a stirred solution of 7.5 parts of 2-aminobenzothiazole in 80 parts of acetonitrile are added 11.75 parts of 2-bromo-1-(4-chlorophenyl)ethanone and the whole is stirred for about 20 hours at room temperature. The precipitated product is filtered off, washed with acetonitrile, and dried, yielding 11.4 parts of 1-(4-chlorophenyl)-2-(2-imino-3(2H)-benzothiazolyl)ethanone hydrobromide; mp. 261°–272° C.

To a stirred suspension of 12.5 parts of 1-(4-chlorophenyl)-2-(2-imino-3(2H)-benzothiazolyl)ethanone hydrobromide in 160 parts of methanol and 100 parts of water are added portionwise 1.25 parts of sodium borohydride while cooling in an ice-bath. Upon completion, stirring is continued for 1 h. 30 at room temperature. The reaction mixture is evaporated in vacuo and the residue is distilled. The formed precipitate is sucked off, washed with water and dissolved in trichloromethane. The water is separated and the solution is dried and evaporated. The residue is crystallized from a mixture of methylbenzene and petroleumether, yielding 8.9 parts of α-(4-chlorophenyl)-2-imino-3(2H)-benzothiazoleethanone; mp. 114° C.

Example II

To a stirred and cooled (0°–5° C.) mixture of 110 parts of concentrated nitric acid solution and 314 parts of concentrated sulfuric acid solution are added dropwise 60 parts of 1,2-dichloro-4-nonylbenzene. Upon completion, stirring is continued for 30 minutes at 0° C. The reaction mixture is poured onto crushed ice and the product is extracted with 2,2'-oxybispropane. The extract is washed successively with water and a sodium hydrogen carbonate solution, dried, filtered and evaporated, yielding 70 parts (100%) of 1,2-dichloro-4-nitro-5-nonylbenzene as an oily residue.

Example III

To a stirred and refluxing mixture of 11.2 parts of iron, 100 parts of ammonium chloride solution 0.8 N and 20 parts of methylbenzene are added 10.5 parts of (4-chloro-3-nitrophenyl)phenylmethanone and the whole is further stirred at reflux temperature for one hour. Methylbenzene (80 parts) is added and the whole is filtered over Hyflo. The organic layer is separated, dried, filtered and evaporated. The residue is washed with cyclohexane, yielding 8.4 parts of (3-amino-4-chlorophenyl)phenylmethanone; mp. 91.9° C.

Example IV

A mixture of 120 parts of 1,2-dichloro-4-nitro-5-nonylbenzene, 2 parts of zinc chloride solution, 83 parts of sodium acetate and 480 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. The residue is dissolved in water and the solution is alkalized with ammonium hydroxide. The product is extracted with 2,2'-oxybispropane. The extract is washed with water, dried, filtered and evaporated. The residue is distilled, yielding 59 parts of 2-nonylbenzenamine; bp. 131°–132° C. at 0.2 mm pressure.

Example V

A mixture of 34 parts of 1-(4-methyl-3-nitrophenyl)1-butanone, 24 parts of 2-propanol saturated with hydrochloric acid and 400 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. Water is added to the residue and the whole is alkalized with ammonium hydroxide. The product is extracted with 2,2'-oxybispropane. The extract is dried, filtered and evaporated, yielding 25.5 parts of 5-butyl-2-methylbenzenamine as a residue.

Example VI

A mixture of 100 parts of 2-chloro-5-(1,1-dimethylethyl)-1,3-dinitrobenzene and 800 parts of methanol is hydrogenated at normal pressure and at room temperature with 10 parts of ruthenium-on-charcoal catalyst 10%. After the calculated amount of hydrogen is taken up, the catalyst is filtered off and the filtrate is evaporated. The residue is purified by column-chromatography over silica gel using trichloromethane as eluent. The pure fractions are collected and the eluent is evaporated, yielding 69 parts (78%) of 2-chloro-5-(1,1-dimethylethyl)-3-nitrobenzenamine as a residue.

Example VII

A mixture of 50 parts of 2-chloro-5-nitrobenzenamine, 33.4 parts of methanethial and 450 parts of 1,4-dioxane is stirred and refluxed for 4 hours. The reaction mixture is evaporated, yielding 62.2 parts of 1-chloro-2-isothiocyanato-4-nitrobenzene as a residue.

Example VIII

A mixture of 17 parts (3-amino-4-chlorophenyl) phenylmethanone, 9.5 parts of carbonothioic dichloride and 200 parts of 1,4-dioxane is stirred and refluxed for 15 minutes. The reaction mixture is evaporated and the oily residue is crystallized from 2,2'-oxybispropane. The product is filtered off and dried, yielding 17 parts (85%) of (4-chloro-3-isothiocyanatophenyl)phenylmethanone; mp. 96.7° C.

In a similar manner there are also prepared:
1-isothiocyanato-2-nonylbenzene as a residue;
4-butyl-2-isothiocyanato-1-methylbenzene as a residue;
2-chloro-1-isothiocyanato-3-nitrobenzene as a residue;

2-chloro-5-(1,1-dimethylethyl)-1-isothiocyanato-3-nitrobenzene; mp. 46.4° C.;
1-cyclohexyl-4-isothiocyanatobenzene as an oily residue; and
1-(4-isothiocyanatophenyl)nonane as a residue.

EXAMPLE IX

To a stirred suspension of 29 parts of 1-chloro-4-isothiocyanato-2-nitrobenzene in 120 parts of ethanol 95% are added dropwise 8.2 parts of 2-aminoethanol (exothermic reaction: temp. rises from 25° to 32° C.). Upon completion, stirring is continued for 30 minutes at room temperature. The precipitated product is filtered off (after cooling to 10° C.) and dried, yielding 30.7 parts (82.5%) of N-(2-chloro-5-nitrophenyl)-N'-(2-hydroxyethyl)thiourea; mp. 158.4° C.

Example X

Following the procedure described in Example IX and using equivalent amounts of the appropriate starting materials there are also prepared:

$$R^a\text{—NH—}\overset{\overset{S}{\|}}{C}\text{—NH—}\underset{}{\text{C}_6\text{H}_4}\text{—}R^b$$

| $R^a$ | $R^b$ | Melting point in °C. |
|---|---|---|
| CH₂CH₂OH | 2-Cl,5-COC₆H₅ | 156.7 |
| CH₂CH₂OH | 4-C₄H₉ | 93.9 |
| CH₂CH₂OH | 2-NO₂ | 133.0 |
| CH₂CH₂OH | 4-O—C₆H₅ | 118.8 |
| C(CH₃)₂CH₂OH | 2-Cl,5-NO₂ | 170.0 |
| CH₂CH₂OH | 2,3-(CH₂)₄ | 157.6 |
| CH₂CH₂OH | 2-C₃H₇ | 110.9 |
| CH₂CH₂OH | 4-CH(CH₃)₂ | 145.3 |
| CH₂CH₂OH | 3,4-(CH₃)₂ | 150.2 |
| CH₂CH₂OH | 3,4-(CH₃)₂ | 151.6 |
| CH₂CH₂OH | 4-C₂H₅ | 135.3 |
| CH₂CH₂OH | 3-C₄H₉ | ±70 |
| CH₂CH₂OH | 3-C₃H₇ | ±80 |
| CH₂CH₂OH | 2-CH₃,5-CH(CH₃)₂ | — |
| CH₂CH₂OH | 4-C(CH₃)₃ | 158.3 |
| CH₂CH₂OH | 3-C₂H₅ | 100.1 |
| CH₂CH₂OH | 2-C₄H₉ | 69.0 |
| CH₂CH₂OH | 3-C(CH₃)₃ | — |
| CH₂CH₂OH | 2-C₉H₁₉ | — |
| CH₂CH₂OH | 3,4-(CH₂)₄ | 136.2 |
| CH₂CH₂OH | 2,5-(CH₃)₂ | 158.3 |
| CH₂CH₂OH | 3-C₅H₁₁ | 80.0 |
| CH₂CH₂OH | 4-C₃H₇ | — |
| CH₂CH₂OH | 2-CH₃,5-C(CH₃)₃ | 92.0 |
| CH₂CH₂OH | 2-CH₃,5-F | 104.0 |
| CH₂CH₂OH | 4-C₆H₁₃ | — |
| CH₂CH₂OH | 3-C₆H₁₃ | — |
| CH₂CH₂OH | 4-O—C₂H₅ | 157.6 |
| CH₂CH₂OH | 2-Cl,5-NO₂ | — |
| CH₂CH₂OH | 2-Cl,3-NO₂ | ±170 |
| CH₂CH₂OH | 2,4,5-(CH₃)₃ | 167.7 |
| CH₂CH₂OH | 2-CH₃,5-C₄H₉ | — |
| CH₂CH₂OH | 2-Cl,3-NO₂,5-C(CH₃)₃ | — |
| CH₂CH(CH₃)OH | 2-Cl,5-NO₂ | 139.0 |
| CH(C₆H₅)CH₂OH | — | 160.8 |
| CH₂CH₂OH | 4-c.C₆H₁₁ | 176.5 |
| CH(C₆H₅)CH₂OH | 4-C₃H₇ | 156.6 |
| CH₂CH₂OH | 4-C₉H₁₉ | 98.4 |
| CH(C₆H₅)CH₂OH | 4-C₆H₁₃ | 147.7 |
| | | 115.8 |
| CH₂—CH{CH₂O—C₆H₄—CH(CH₃)₃}OH | 4-C(CH₃)₃ | 140.3 |
| CH₂—CH{CH₂O—C₆H₄—CH(CH₃)₃}OH | — | 148.9 |
| CH₂—CH{CH₂O—C₆H₄—CH₃}OH | 4-Cl | 138.8 |
| CH₂—CH{CH₂O—C₆H₄—F}OH | 4-C(CH₃)₃ | 120.1 |
| CH₂—CH{CH₂O—C₆H₄—F}OH | | |

-continued $$R^a-NH-\overset{\overset{S}{\|}}{C}-NH-\underset{}{\underset{}{\bigcirc}}-R^b$$

| $R^a$ | $R^b$ | Melting point in °C. |
|---|---|---|
| CH₂—CH(CH₂O—⟨C₆H₃Cl⟩)OH | 4-Cl | 144.0 |
| CH₂—CH(C₆H₅)OH | — | 129.1 |

Example XI

To a stirred mixture of 6.4 parts of N-(4-fluorophenyl)-N'-(2-hydroxyethyl)thiourea and 80 parts of tetrachloromethane is added dropwise a solution of 4.8 parts of bromine in 40 parts of tetrachloromethane between 20° and 25° C. Upon completion, stirring is continued for 1 hour at reflux temperature. The reaction mixture is cooled to room temperature. The precipitated product is filtered off, washed with acetonitrile and dried, yielding 5.8 parts of 2-[(6-fluoro-2-benzothiazolyl)amino]ethanol monohydrobromide; mp. 163.6° C.

Example XII

Following the procedure described in Example XI and starting from the corresponding thiourea there are also prepared:

$$R^a-NH-\underset{N}{\overset{S}{\underset{}{\bigcirc}}}-R^b$$

| $R^a$ | $R^b$ | Salt or Base | Melting point in °C. |
|---|---|---|---|
| CH₂CH₂OH | 6-Cl | — | 138.1 |
| CH₂CH₂OH | 4-Cl | — | 102.2 |
| CH₂CH₂OH | 6-C₄H₉ | — | 90.9 |
| CH₂CH₂OH | 4-NO₂ | — | 143.0 |
| CH₂CH₂OH | 6-CH₃ | — | 131.6 |
| CH₂CH₂OH | 6-OCH₃ | — | 131.0 |
| C(CH₃)₂CH₂OH | 5-NO₂ | — | 199.0 |
| CH₂CH₂OH | 4,5-(CH₂)₄ | — | 118.2 |
| CH₂CH₂OH | 4-C₃H₇ | — | 120.0 |
| CH₂CH₂OH | 4-CH₃ | — | 107.9 |
| CH₂CH₂OH | 5-CH₃ | — | ±100 |
| CH₂CH₂OH | 5,6-(CH₃)₂ | — | 186.7 |
| CH₂CH₂OH | 6-CH(CH₃)₂ | HBr | 128.8 |
| CH₂CH₂OH | 6-C₂H₅ | — | 115.1 |
| CH₂CH₂OH | 5,6-(CH₂)₃ | — | 164.2 |
| CH₂CH₂OH | 5-C₄H₉ | — | — |
| CH₂CH₂OH | 5,6-(CH=CH—CH=CH) | — | 166.6 |
| CH₂CH₂OH | 5-C₃H₇ | — | 72.8 |
| CH₂CH₂OH | 4-CH₃,7-CH(CH₃)₂ | — | 127.9 |
| CH₂CH₂OH | 4,5-(CH=CH—CH=CH) | — | — |
| CH₂CH₂OH | 4-CH(CH₃)₂ | HBr | 150.7 |
| CH₂CH₂OH | 5-C₂H₅ | HBr | 177.5 |
| CH₂CH₂OH | 4-C₄H₉ | — | 77.1 |
| CH₂CH₂OH | 5-C(CH₃)₃ | HBr | 97.0 |
| CH₂CH₂OH | 6-O—C₆H₅ | HCl | 146.4 |
| CH₂CH₂OH | 4-C₉H₁₉ | HBr | 128.2 |
| CH₂CH₂OH | 6-C(CH₃)₃ | HBr | — |
| CH₂CH₂OH | 4,7-(CH₃)₂ | HBr | 182.3 |
| CH₂CH₂OH | 5-C₅H₁₁ | — | — |
| CH₂CH₂OH | 5,6-(CH₂)₄ | HBr | 184.4 |
| CH₂CH₂OH | 6-C₃H₇ | — | — |
| CH₂CH₂OH | 4-C₂H₅ | — | 101.1 |
| CH₂CH₂OH | 4-CH₃,7-C(CH₃)₃ | — | — |
| CH₂CH₂OH | 4-CH₃,7-F | HBr | 160.3 |
| CH₂CH₂OH | 6-C₆H₁₃ | — | — |
| CH₂CH₂OH | 5-C₆H₁₃ | — | — |
| CH₂CH₂OH | 6-OC₂H₅ | — | 127.0 |
| CH₂CH₂OH | 4,6,7-(CH₃)₃ | — | 135.6 |
| CH₂CH₂OH | 4-CH₃,7-C₄H₉ | — | — |
| CH₂CH₂OH | 6-c . C₆H₁₁ | ½H₂O | 141.1 |
| CH(C₆H₅)CH₂OH | — | — | 166.2 |

-continued

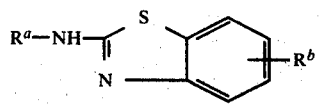

| $R^a$ | $R^b$ | Salt or Base | Melting point in °C. |
|---|---|---|---|
| CH₂CH(OH)—CH₂O(4-Br—C₆H₄) | — | — | 144.6 |
| CH(C₆H₅)CH₂OH | 6-C₃H₇ | — | 161.9 |
| CH(C₆H₅)CH₂OH | 6-C₆H₁₃ | — | 112.7 |
| CH₂CH₂OH | 6-C₉H₁₉ | — | 100.9 |
| CH₂CH(OH)—CH₂O(4-C(CH₃)₃—C₆H₄) | — | — | 162.5 |
| (CH₂CH(OH)—CH₂O(4-C(CH₃)₃—C₆H₄) | 6-C(CH₃)₃ | — | 194.4 |
| CH₂CH(OH)—CH₂O(4-F—C₆H₄) | 6-Cl | — | 161.1 |
| CH₂CH(OH)—CH₂O(4-F—C₆H₄) | 6-C(CH₃)₃ | — | 162.3 |
| CH₂CH(OH)—CH₂O(2-Cl—C₆H₄) | 6-Cl | — | 134.0 |
| CH₂CH(OH)—CH₂O(4-CH₃—C₆H₄) | — | — | 128.7 |
| CH₂CH(OH)—CH₂O(2-Cl—C₆H₄) | — | — | — |

Example XIII

A mixture of 116 parts of N-(2-chloro-5-nitrophenyl)-N'-(2-hydroxy-1-phenylethyl)thiourea, 50 parts of potassium carbonate and 675 parts of N,N-dimethylacetamide is stirred and refluxed for 1 hour. The reaction mixture is poured onto 2000 parts of water. After cooling, the whole is filtered over Hyflo and the product is allowed to crystallize from the filtrate. It is filtered off and dried, yielding 23 parts of β-(5-nitro-2-benzothiazolylamino)benzeneethanol.

In a similar manner there is also prepared:
2-(7-nitro-2-benzothiazolylamino)ethanol; mp. 176.8° C.

Example XIV

A mixture of 28 parts of N-(2-chloro-5-nitrophenyl)N'-(2-hydroxyethyl)thiourea, 14.5 parts of potassium carbonate and 225 parts of N,N-dimethylformamide is stirred and refluxed for one hour. After cooling, 300 parts of water are added. The precipitated product is filtered off, washed with water and dried, yielding 20.5 parts (82%) of 2-[(5-nitro-2-benzothiazolyl)amino]ethanol; mp. 183.4° C.

In a similar manner there are also prepared:
2-{[5-(1,1-dimethylethyl)-7-nitro-2-benzothiazolyl]amino}ethanol; mp. 200.7° C.; and
1-[(5-nitro-2-benzothiazolyl)amino]-2-propanol; mp. 200° C.

Example XV

A mixture of 6 parts of N-(5-benzoyl-2-chlorophenyl)N'-(2-hydroxyethyl)thiourea, 2.5 parts of sodium hydride dispersion 75% and 90 parts of N,N-dimethylacetamide is stirred and heated quickly to 130° C. The reaction mixture is cooled, water is added and the whole is allowed to stand overnight. The precipitated product is filtered off, washed with water and crystallized from ethanol, yielding 2.8 parts of {2-[(2-hydroxyethyl)amino]-5-benzothiazolyl}phenylmethanone; mp. 159° C.

PREPARATION OF FINAL COMPOUNDS

Example XVI

To a stirred and cooled (0° C.) solution of 19 parts of 2-[(5-nitro-2-benzothiazolyl)amino]ethanol in 18 parts of N,N-dimethylformamide is added dropwise (slowly) a solution of 10.7 parts of thionyl chloride in 207 parts of N,N-dimethylformamide. Upon completion, the mixture is stirred and heated slowly to reflux and stirring at reflux is continued for 4 hours. After cooling, the precipitated product is filtered off and washed with N,N-dimethylformamide and 2,2'-oxybispropane, yielding 17.5 parts (85%) of 2,3-dihydro-6-nitroimidazo[2,1-b]benzothiazole monohydrochloride; mp. 314°–316° C. (dec.).

Example XVII

Following the cyclization-procedure described in Example XVI and starting from an appropriately substituted 2-[(2-benzothiazolyl)amino]ethanol there are also prepared:

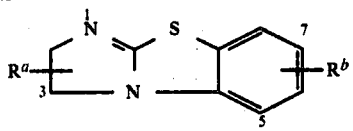

| $R^a$ | $R^b$ | Salt or Base | Melting point in °C. |
|---|---|---|---|
| — | — | HCl | 231.0 |
| — | 6-CO—C6H5 | HCl | 267.0 |
| — | 7-F | — | 98.8 |
| — | 7-Cl | — | 179.9 |
| — | 5-Cl | — | 166.3 |
| — | 5-NO2 | HCl | 263.3 |
| — | 7-n . C4H9 | HCl . ½H2O | 135.2 |
| — | 7-CH3 | HCl | +300° C. |
| — | 7-OCH3 | HCl | 222.7 |
| 2-CH3,2-CH3 | 6-NO2 | — | 217.0 |
| — | 5,6-(CH2)4 | HCl | 287.6 |
| — | 6-CH3 | HCl | +300 |
| — | 5-n . C3H7 | HCl | 221.2 |
| — | 5-CH3 | HCl | 293.4 |
| — | 6-CH3,7-CH3 | HCl | 292.1 |
| — | 7-i . C3H7 | (COOH)2 | 183.9 |
| — | 7-C2H5 | HCl | 198.9 |
| — | 6-n . C4H9 | HCl . ½H2O | 207.8 |
| — | 6,7-(CH2)3 | HCl | 295–312 |
| — | 6-n . C3H7 | HCl | 232.4 |
| — | 6,7-(CH=CH—CH=CH) | HCl | 237.0 |
| — | 5-CH3,8-i . C3H7 | HCl | 229.1 |
| — | 5,6-(CH=CH—CH=CH) | HCl | 296.3 |
| — | 5-n . C4H9 | HCl | 225.6 |
| — | 5-i . C3H7 | HCl | 271.2 |
| — | 6-t . C4H9 | HCl | 256.1 |
| — | 7-O—C6H5 | HCl | 222.4 |
| — | 5-n . C9H19 | — | 79.2 |
| — | 7-t . C4H9 | — | 120.3 |
| — | 6-C2H5 | HCl | 242.2 |
| — | 5-CH3,8-CH3 | HCl | +300 |
| — | 6-n . C5H11 | HCl | 193.4 |
| — | 5-CH3,8-t . C4H9 | — | 145.6 |
| — | 6,7-(CH2)4 | — | 116.1 |
| — | 7-n . C3H7 | HCl | 164.6 |
| — | 5-CH3,8-F | HCl | 282.3 |
| — | 5-C2H5 | HCl | 239.1 |
| — | 7-n . C6H13 | HCl ½H2O | 144.6 |
| — | 6-n . C6H13 | HCl | 154.2 |
| — | 7-O—C2H5 | — | 88.3 |
| 2-C6H5 | 6-NO2 | HCl | 258.4 |
| — | 8-NO2 | — | 182.4 |
| — | 5-CH3,7-CH3,8-CH3 | — | 154.8 |
| — | 5-CH3,8-n . C4H9 | — | 64.0 |
| — | 6-t . C4H9,8-NO2 | — | 200.0 |
| 3-CH3 | 6-NO2 | — | — |
| — | 7-C6H5 | — | 114.9 |
| 3-CH2O(4-Br—C6H4) | — | HCl | 224.7 |
| 2-C6H5 | 7-n . C4H9 | HCl | 220.5 |
| 3-CH2O(4-t . C4H9—C6H4) | — | — | 110.8 |
| 2-C6H5 | — | — | 97.0 |
| 3-CH2O(4-F—C6H4) | 7-Cl | — | 139.0 |
| 2-C6H5 | 7-n . C6H13 | HCl | 179.7 |
| — | 7-n . C9H19 | HCl | 152.9 |
| 2-CH2O(4-t . C4H9—C6H4) | 7-t . C4H9 | HCl | 265.2 |
| 3-CH2O(4-CH3—C6H4) | — | HCl | 202.2 |
| 3-CH2O(2-Cl—C6H4) | 7-Cl | — | 175.4 |
| 3-CH2O(4-F—C6H4) | 7-t . C4H9 | — | 137.1 |
| 3-CH2O(2-Cl—C6H4) | — | — | 132.6 |

Example XVIII

A mixture of 4 parts of α-(4-chlorophenyl)2-imino-3-benzothiazolineethanol and 23 parts of concentrated sulfuric acid is stirred first for 30 minutes in an ice-bath and further for 1 h. 30 at room temperature. The reaction mixture is poured onto crushed ice, alkalized with ammonium hydroxide and the product is extracted with trichloromethane. The extract is dried, filtered and evaporated. The solid residue is crystallized from 2-propanol, yielding 1.6 parts of 2-(4-chlorophenyl)-2,3-dihydroimidazo[2,1-b]benzothiazole; mp. 143.3° C.

Example XIX

A mixture of 50 parts of N-(2-hydroxy-2-phenylethyl)N'-phenylthiourea, 30 parts of bromine and 800 parts tetrachloromethane is stirred and refluxed for 2 hours. The reaction mixture is evaporated. From the residue, the free base is liberated in the conventional manner with ammonium hydroxide and extracted with trichloromethane. The extract is dried, filtered and evaporated. The residue is suspended in boiling 4-methyl-2-pentanone. The product is filtered off and stirred in a diluted sodium hydroxide solution. The product is extracted with 4-methyl-2-pentanone. The extract is washed with water, dried, filtered and evaporated. The residue is crystallized from acetonitrile. The product is filtered off and dried, yielding 10 parts (22%) of 2,3-dihydro-3-phenylimidazo[2,1-b]benzothiazole; mp. 131.7° C.

Example XX

To a stirred solution of 95 parts of 2,3-dihydroimidazo[2,1-b]benzothiazole in 480 parts of 2-propanol are added 57 parts of nitric acid solution 66%. The formed nitrate salt is filtered off and dried, yielding 129 parts (100%) of 2,3-dihydroimidazo[2,1-b]benzothiazole mononitrate; mp. 163.7° C.

Example XXI

10 Parts of 2,3-dihydroimidazo[2,1-b]benzothiazole mononitrate are added portionwise to 55.2 parts of concentrated sulfuric acid at 0° C. Upon completion, stirring is continued for 30 minutes at room temperature. The reaction mixture is poured onto crushed ice and the whole is alkalized with ammonium hydroxide at a temperature below 20° C. The product is extracted with a mixture of trichloromethane and methanol (90:10 by volume). The extract is washed with water, dried, filtered and evaporated. The residue is crystallized from 160 parts of 1-butanol. The product is filtered off and dried, yielding 8 parts (80%) of 2,3-dihydro-7-nitroimidazol[2,1-b]benzothiazole; mp. 238.9° C.

In a similar manner there are also prepared:

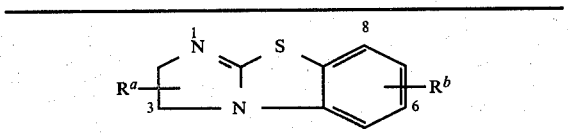

| $R^a$ | $R^b$ | Salt or base | Melting point in °C. |
|---|---|---|---|
| — | 5-CH$_3$, 7-NO$_2$, 8-i . C$_3$H$_7$ | — | 139.2 |
| — | 6-NO$_2$, 7-n . C$_6$H$_{13}$ | — | 95.7 |
| — | 5-CH$_3$, 7-NO$_2$, 8-CH$_3$ | — | 207.6 |
| — | 6-NO$_2$, 7-C$_2$H$_5$ | — | 176.9 |
| — | 6-NO$_2$, 7-n . C$_3$H$_7$ | — | — |
| — | 6-NO$_2$, 7-n . C$_4$H$_9$ | — | 123–125 |
| — | 5-CH$_3$, 6-NO$_2$, 7-CH$_3$, 8-CH$_3$ | — | 217.0 |
| — | 6-NO$_2$, 7-CH$_3$ | — | 233.6 |

Example XXII

A mixture of 11 parts of 2,3-dihydro-6-nitroimidazo[2,1-b]benzothiazole and 80 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. The residue is crystallized from dimethylbenzene. The product is filtered off and dried, yielding 5.6 parts of 2,3-dihydroimidazo[2,1-b]benzothiazol-6-amine; mp. 204°–210° C.

Following the same nitro-to-amine reduction there is also prepared:
2,3-dihydroimidazo[2,1-b]benzothiazol-7-amine; mp. 212°–216° C.

Example XXIII

A mixture of 5.5 parts of 2,3-dihydro-5-nitroimidazo[2,1-b]benzothiazole and 160 parts of methanol, saturated with ammonia is hydrogenated at normal pressure and at room temperature with 2 parts of platinum-on-charcoal catalyst 5%. After the calculated amount of hydrogen is taken up, the catalyst is filtered off and the filtrate is evaporated. The residue is crystallized from 1-butanol. The product is filtered off and dried, yielding 3 parts of 2,3-dihydroimidazo[2,1-b]benzothiazol-5-amine; mp. 229.2° C.

In a similar manner there are also prepared:

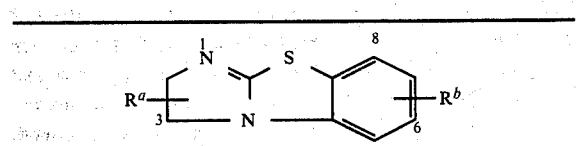

| $R^a$ | $R^b$ | Salt or base | Melting point in °C. |
|---|---|---|---|
| 2-CH$_3$, 2-CH$_3$ | 6-NH$_2$ | — | 198.0 |
| — | 5-CH$_3$, 7-NH$_2$, 8-i . C$_3$H$_7$ | — | 263.0 |
| — | 6-NH$_2$, 7-n . C$_6$H$_{13}$ | — | 136.6 |
| — | 5-CH$_3$, 7-NH$_2$, 8-CH$_3$ | — | — |
| 2-C$_6$H$_5$ | 6-NH$_2$ | — | — |
| — | 8-NH$_2$ | — | 199.0 |
| — | 6-NH$_2$, 7-C$_2$H$_5$ | — | 235–242 |
| — | 6-NH$_2$, 7-n . C$_3$H$_7$ | — | 181–185.4 |
| — | 6-NH$_2$, 7-n . C$_4$H$_9$ | — | 153.1 |
| — | 6-t . C$_4$H$_9$, 8-NH$_2$ | — | 170.0 |
| — | 6-NH$_2$, 7-CH$_3$ | — | 226.3 |
| 3-CH$_3$ | 6-NH$_2$ | 2HCl . ½H$_2$O | 279.2 |

Example XXIV

A mixture of 5.5 parts of imidazo[2,1-b]benzothiazol-6-amine and 7.5 parts of diethyl 2-(ethoxymethylene)propanedioate is stirred for 30 minutes at 110° C. The solid product is suspended in 1,1'-oxybisethane. It is filtered off and dried, yielding 10 parts (95%) of diethyl 2-[(2,3-dihydroimidazo[2,1-b]benzothiazol-6-yl)aminomethylene]propanedioate; mp. 140° C.

In a similar manner the following compounds are prepared starting from an appropriate amine and diethyl-2-(ethoxymethylene)propanedioate:
diethyl 2-[(2,3-dihydroimidazo[2,1-b]benzothiazol-7-yl-amino)methylene]propanedioate; mp. 156.1° C.;
diethyl 2-{[2,3-dihydro-5-methyl-8-(1-methylethyl)imidazo[2,1-b]benzothiazol-7-yl]aminomethylene}-propanedioate; mp. 142.3° C.;
diethyl 2-[(7-ethyl-2,3-dihydroimidazo[2,1-b]benzothiazol-6-yl)aminomethylene]propanedioate hemihydrate; mp. 133.7° C.;
diethyl 2-[(7-butyl-2,3-dihydroimidazo[2,1-b]benzothiazol-6-yl)aminomethylene]propanedioate; mp. 133.2° C.;
diethyl 2-[(2,3-dihydroimidazo[2,1-b]benzothiazol-8-yl)aminomethylene]propanedioate; mp. 142.7° C.;
diethyl 2-[(2,3-dihydro-7-methylimidazo[2,1-b]benzothiazol-6-ylamino)methylene]propanedioate; mp. 180.5° C.;
diethyl 2-{[6-(1,1-dimethylethyl)-2,3-dihydroimidazo[2,1-b]benzothiazol-8-yl]aminomethylene}propanedioate; mp. 151.5° C.;
diethyl 2-[(7-hexyl-2,3-dihydroimidazo[2,1-b]benzothiazol-6-ylamino)methylene]propanedioate; mp. 99.8° C.; and diethyl 2-[(2,3-dihydro-3-methylimidazo[2,1-b]benzo-thiazol-6-ylamino)methylene]propanedioate; mp. 110° C.

Example XXV

To a stirred solution of 10 parts of diethyl 2-[(2,3-dihydroimidazo[2,1-b]benzothiazol-6yl)aminomethylene]propanedioate in 100 parts of hexamethylphosphoric triamide are added portionwise 1.1 parts of sodium hydride dispersion 76.1%:exothermic reaction (temp. rises to 36° C.). After stirring for 30 minutes at room temperature, 5.55 parts of diethyl sulfate are added dropwise. Upon completion, stirring is continued first for 8 hours at 40° C. and further overnight at room temperature. 450 Parts of methylbenzene are added and the whole is washed three times with 200 parts of water. The organic phase is dried, filtered and evaporated, yielding 12 parts of diethyl 2-{[(2,3-dihydroimidazo[2,1-b]benzothiazol-6-yl)ethylamino]methylene}propanedioate as an oily residue.

Following the same procedure and using equivalent amounts of the appropriate starting materials there are prepared:

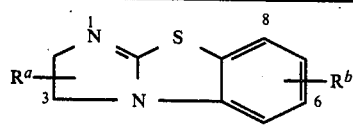

| $R^a$ | $R^b$ | Salt or base | Melting point in °C. |
|---|---|---|---|
| — | 7-N(n . C$_3$H$_7$)—CH=C(COOC$_2$H$_5$)$_2$ | — | 103.0 |
| — | 7-N(CH$_3$)—CH=C(COOC$_2$H$_5$)$_2$ | — | — |
| — | 6-N(CH$_3$)—CH=C(COOC$_2$H$_5$)$_2$ | — | 141.7 |
| — | 6-N(nC$_3$H$_7$)—CH=C(COOC$_2$H$_5$)$_2$ | — | 145.6 |
| — | 7-N(CH$_2$C≡CH)—CH=C(COOC$_2$H$_5$)$_2$ | — | 120.0 |
| — | 7-N(C$_2$H$_5$)—CH=C(COOC$_2$H$_5$)$_2$ | — | — |
| — | 7-N(n . C$_4$H$_9$)CH=C(COOC$_2$H$_5$)$_2$ | — | — |
| — | 7-N(n . C$_6$H$_{13}$)CH=C(COOC$_2$H$_5$)$_2$ | — | — |
| — | 7-N(C$_2$H$_5$)CH=C(COOC$_2$H$_5$)$_2$; 5-CH$_3$; 8-i . C$_3$H$_7$ | — | — |
| — | 6-N(CH$_3$)CH=C(COOC$_2$H$_5$)$_2$; 7-C$_2$H$_5$ | — | — |
| — | 6-N(C$_2$H$_5$)CH=C(COOC$_2$H$_5$)$_2$; 7-C$_2$H$_5$ | — | — |
| — | 6-N(CH$_3$)CH=C(COOC$_2$H$_5$)$_2$; 7-n . C$_4$H$_9$ | — | — |
| — | 8-N(C$_2$H$_5$)CH=C(COOC$_2$H$_5$)$_2$ | — | — |
| — | 6-N(C$_2$H$_5$)CH=C(COOC$_2$H$_5$)$_2$; 7-n . C$_4$H$_9$ | — | — |
| — | 6-N(C$_2$H$_5$)CH=C(COOC$_2$H$_5$)$_2$; 7-CH$_3$ | — | — |
| — | 8-N(C$_2$H$_5$)CH=C(COOC$_2$H$_5$)$_2$; 6-t . C$_4$H$_9$ | — | — |
| — | 6-N(CH$_3$)CH=C(COOC$_2$H$_5$)$_2$; 7-CH$_3$ | — | — |
| — | 6-N(CH$_3$)CH=C(COOC$_2$H$_5$)$_2$; 7-n . C$_5$H$_{11}$ | — | — |
| — | 6-N(C$_2$H$_5$)CH=C(COOC$_2$H$_5$)$_2$; 7-n . C$_6$H$_{13}$ | — | — |
| — | 6-N(n . C$_3$H$_7$)CH=C(COOC$_2$H$_5$)$_2$; 7-CH$_3$ | — | — |
| 3-CH$_3$ | 6-N(CH$_3$)CH=C(COOC$_2$H$_5$)$_2$ | — | — |
| 3-CH$_3$ | 6-N(C$_2$H$_5$)CH=C(COOC$_2$H$_5$)$_2$ | — | — |

Example XXVI

A mixture of 12 parts of diethyl 2-{[(2,3-dihydroimidazo[2,1-b]benzothiazol-6-yl)ethylamino]methylene}propanedioate, 36 parts of concentrated hydrochloric acid and 30 parts of water is stirred and refluxed for 15 minutes. The reaction mixture is cooled and alkalized with ammonium hydroxide. The product is extracted with methylbenzene. The extract is washed with water, dried, filtered and evaporated. The residue is crystallized from 4-methyl-2-pentanone. The product is filtered off and dried, yielding 2 parts of N-ethyl-2,3-dihydroimidazo[2,1-b]benzothiazol-6-amine; mp. 239°–246° C.

In a similar manner there are also prepared:

| $R^a$ | $R^b$ | Salt or base | Melting point in °C. |
|---|---|---|---|
| — | 7-NH-n . C$_3$H$_7$ | — | 173.4–175.4 |
| — | 7-NH—CH$_3$ | — | 207.5 |
| — | 6-NH-n . C$_3$H$_7$ | — | 153.4 |
| — | 6-NH—CH$_3$ | — | 218.3 |
| — | 7-NH—CH$_2$—C≡CH | — | 146.6 |
| — | 7-NH—C$_2$H$_5$ | — | 186.4 |
| — | 7-NH-n . C$_4$H$_9$ | — | 147.5 |
| — | 7-NH-n . C$_6$H$_{13}$ | — | 133.1 |
| — | 5-CH$_3$, 7-NH—C$_2$H$_5$, 8-i . C$_3$H$_9$ | — | 136.2 |
| — | 6-NH—CH$_3$, 7-C$_2$H$_5$ | — | 233.4 |
| — | 6-NH—C$_2$H$_5$, 7-C$_2$H$_5$ | — | 137.2 |
| — | 6-NH—CH$_3$, 7-n . C$_4$H$_9$ | — | 147.1 |
| — | 8-NH—C$_2$H$_5$ | — | 144.0 |
| — | 6-NH—C$_2$H$_5$, 7-n . C$_4$H$_9$ | — | 116.3 |
| — | 6-NH—C$_2$H$_5$, 7-CH$_3$ | — | 199.7 |
| — | 6-t . C$_4$H$_9$, 8-NH—C$_2$H$_5$ | — | 168.4 |
| — | 6-NH—CH$_3$, 7-CH$_3$ | — | 263.7 |
| — | 6-NH—CH$_3$, 7-n . C$_6$H$_{13}$ | — | 136.4 |
| — | 6-NH—C$_2$H$_5$, 7-n . C$_6$H$_{13}$ | — | 80.7 |
| — | 6-NH-n . C$_3$H$_7$, 7-CH$_3$ | — | 119.4 |
| 3-CH$_3$ | 6-NH—CH$_3$ | — | 144.9 |
| 3-CH$_3$ | 6-NH—C$_2$H$_5$ | — | 124.9 |

Example XXVII

To a stirred mixture of 4 parts of imidazo[2,1-b]benzothiazol-6-amine and 30 parts of acetic acid are added 1.6 parts of 2-propanone. After stirring for 10 minutes at room temperature, 0.6 parts of sodium borohydride are added portionwise at 20° C. (cooling is necessary). Upon completion, stirring is continued for 10 minutes. The reaction mixture is poured onto water and the whole is alkalized to pH 7–8 with ammonium hydroxide. The product is extracted with trichloromethane. The extract is washed with water, dried, filtered and evaporated. The residue is purified by column-chromatography over silica gel using a mixture of trichloromethane and methanol (95:5 by volume), saturated with ammonia, as eluent. The pure fractions are collected and the eluent is evaporated. The residue is crystallized from 4-methyl-2-pentanone. The product is filtered off and dried, yielding 2.5 parts (54%) of 2,3-dihydro-N-(1-methylethyl)imidazo[2,1-b]benzothiazol-6-amine; mp. 128.2° C.

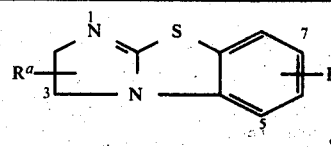

| $R^a$ | $R^b$ | Salt or base | Melting point in °C |
|---|---|---|---|
| — | 6-NH-c . $C_5H_9$ | — | 146.8 |
| — | 6-NH-c . $C_6H_{11}$ | — | 159.3 |
| — | 6-NH—⟨piperidine-N-CH₃⟩ | — | 187.0 |
| — | 7-NH-c . $C_6H_{11}$ | — | 164.1 |
| — | 7-NH-c . $C_5H_9$ | — | 143.7 |
| — | 7-NH—⟨piperidine-N-CH₃⟩ | — | 179.1 |
| — | 7-NH-i . $C_3H_7$ | — | 146.9 |
| — | 7-NH—$CH_2$—$C_6H_5$ | — | 135.5 |
| — | 7-NH-adamantyl | — | 175.0 |
| — | 7-NH-c . $C_7H_{13}$ | 2HCl | 266.5 |
| — | 7-NH—$CH(C_2H_5)_2$ | — | 170.2 |
| — | 7-NH—$CH_2[(3,4,5-(OCH_3)_3—C_6H_2]$ | 2 HCl | 210.8 |
| — | 6-NH—$CH(C_2H_5)_2$ | — | 125.3 |
| — | 7-NH—CH—$(CH_2)_3N(C_2H_5)_2$ \| $CH_3$ | 3HCl . $H_2O$ | 209.1 |
| — | 5-NH—$CH(CH_3)_2$ | HCl | 259.8 |
| — | 7-NH—$CH(CH_3)C_2H_5$ | — | 137.5 |
| — | 7-NH—$CH(CH_3)$n . $C_3H_7$ | — | 112.0 |
| — | 6-NH—$CH(CH_3)$n . $C_3H_7$ | — | 108.5 |
| — | 6-NH—$CH(CH_3)C_2H_5$ | — | 117.4 |
| — | 7-NH—$CH(CH_3)$i . $C_3H_7$ | — | 154.1 |
| — | 7-NH—$CH(CH_3)$n . $C_4H_9$ | — | 106.5 |
| — | 6-NH—$CH_2$—(4-Cl—$C_6H_4$) | — | 178.9 |
| 2-$CH_3$,2-$CH_3$ | 6-NH-i . $C_3H_7$ | HCl | 234.9 |
| — | 7-NH—$CH_2$—$C(CH_3)_3$ | — | 145.3 |
| — | 6-NH—$CH_2$—$C(CH_3)_3$ | — | 158.9 |
| — | 7-NH—$CH_2$—(2,4-$Cl_2$—$C_6H_3$) | 2HCl . ½$H_2O$ | >300 |
| — | 6-NH—$CH_2$(4-$OCH_3$—$C_6H_4$) | — | 165.5 |
| — | 7-NH—$CH_2$(4-$CH_3$—$C_6H_4$) | — | 164.1 |
| — | 6-NH—$CH_2[(3,4,5-(OCH_3)_3$—$C_6H_2]$ | ½$C_2H_5OH$ | 168.0 |
| — | 5-NH—$CH_2[(3,4,5-(OCH_3)_3$—$C_6H_2]$ | — | 142.9 |
| — | 5-$CH_3$, 7-NH-i . $C_3H_7$, 8-i . $C_3H_7$ | — | 125.8 |
| — | 5-$CH_3$, 7-NH-c . $C_5H_9$, 8-i . $C_3H_7$ | 2HCl . 2$H_2O$ | 243.1 |
| — | 5-$CH_3$, 7-NH—$CH(C_2H_5)_2$, 8-i . $C_3H_7$ | 2HCl . 2$H_2O$ | 219.8 |
| — | 5-$CH_3$, 7-NH-i . $C_3H_7$, 8-$CH_3$ | — | 134.1 |
| — | 6-NH-i . $C_3H_7$, 7-n . $C_6H_{13}$ | 2HCl . ½$H_2O$ | 210.6 |
| 2-$C_6H_5$ | 6-NH-i . $C_3H_7$ | — | 133.2 |
| — | 8-NH-i . $C_3H_7$ | — | 133.9 |
| — | 6-NH—$CH(CH_3)CH_2OH$ | — | 227.9 |
| — | 6-NH-c . $C_5H_9$, 7-$C_2H_5$ | — | 126.8 |
| — | 6-NH—$CH(C_2H_5)_2$7-$C_2H_5$ | HCl . ½$H_2O$ | 183.6 |
| — | 6-NH-i . $C_3H_7$, 7-$C_2H_5$ | HCl | 257.0 |
| — | 8-NH—$CH(C_2H_5)_2$ | — | 145.4 |
| — | 6-NH—$CH(CH_3)_2$, 7-n . $C_4H_9$ | — | 51.5 |
| — | 6-NH—$CH(C_2H_5)_2$, 7-n . $C_4H_9$ | — | 69.4 |
| — | 6-NH-c . $C_5H_9$, 7-n . $C_4H_9$ | — | 86.3 |
| — | 6-NH—$CH(C_2H_5)_2$, 7-$CH_3$ | — | 74.7 |
| — | 6-NH-i . $C_3H_7$, 7-$CH_3$ | — | 159.3 |
| — | 6-NH-c . $C_5H_9$, 7-$CH_3$ | — | 156.0 |
| — | 6-NH—$CH(CH_3)CH_2OH$,7-$CH_3$ | — | 204.2 |
| — | 6-t . $C_4H_9$, 7-NH-i . $C_3H_7$ | — | 185.4 |
| — | 6-NH—$CH(CH_3)CH_2OH$,7-$C_2H_5$ | — | 177.5 |
| — | 6-NH—$CH(CH_3)CH_2OH$, 7-n . $C_3H_9$ | — | 161.0 |
| — | 6-NH-c . $C_5H_9$, 7-n . $C_6H_{13}$ | HCl | 208.2 |

-continued

| | | | |
|---|---|---|---|
| $R^a$ | $R^b$ | Salt or base | Melting point in °C. |
| — | 6-NH—CH(C₂H₅)₂, 7-n . C₆H₁₃ | HCl | 177.3 |
| — | 6-NH—CH(CH₃)₂ | 2HCl | 239.6 |

Example XXVIII

To a stirred mixture of 60 parts of trifluoroacetic acid and 4 parts of sodium borohydride are added portionwise, during a 5 hours-period, 4 parts of 2,3-dihydroimidazo[2,1-b]benzothiazol-6-amine at 30°–40° C. The reaction mixture is poured onto 300 parts of ice-water. The precipitated product is filtered off, washed with water and taken up in trichloromethane. The mixture is washed with ammonium hydroxide. The organic phase is dried, filtered and evaporated. The residue is crystallized from acetonitrile, yielding 3.3 parts of 2,3-dihydro-N-(2,2,2-trifluoroethyl)imidazo[2,1-b]benzothiazol-6-amine; mp. 211.7° C.

Example XXIX

To a stirred and cooled mixture of 5 parts of 2,3-dihydro-imidazo[2,1-b]benzothiazol-7-amine and 200 parts of formic acid are added portionwise 9.8 parts of sodium borohydride while nitrogen gas is introduced. Upon completion, stirring is continued first for 1 hour at 40° C. and further overnight at room temperature. The reaction mixture is evaporated and 500 parts of water are added to the residue. The aqueous phase is washed with 4-methyl-2-pentanone and filtered over hyflo. The filtrate is alkalized with ammonium hydroxide and the product is extracted with trichloromethane. The extract is washed with water, dried, filtered and evaporated. The residue is purified by column-chromatography over silica gel using a mixture of trichloromethane and methanol (93:7 by volume), saturated with ammonia, as eluent. The pure fractions are collected and the eluent is evaporated. The residue is crystallized from a mixture of methylbenzene and 2,2'-oxybispropane. The product is filtered off and dried, yielding 2.4 parts of 2,3-dihydro-N,N-dimethylimidazo[2,1-b]benzothiazol-7-amine; mp. 144.3° C.

In a similar manner there are also prepared:
2,3-dihydro-N,N-dipropylimidazo[2,1-b]benzothiazol-7-amine; mp. 82° C.;
N,N-diethyl-2,3-dihydroimidazo[2,1-b]benzothiazol-6-amine; mp. 136.2° C.; and
2,3-dihydro-N,N-dimethylimidazo[2,1-b]benzothiazol-6-amine; mp. 171° C.

Example XXX

To a stirred mixture of 360 parts of formic acid and 7.5 parts of 2,3-dihydroimidazo[2,1-b]benzothiazol-8-amine are added portionwise, during a 2 hours-period, 14.7 parts of sodium borohydride while nitrogen gas is introduced and the temperature is kept at about 30° C. Upon completion, stirring is continued first for 1 hour at about 60° C. and further overnight at room temperature. 200 Parts of water are added to the reaction mixture and the whole is alkalized with ammonium hydroxide at a temperature below 10° C. The product is extracted with warm trichloromethane. The extract is filtered over Hyflo and the filtrate is evaporated. The residue is boiled in 1,1'-oxybisethane. The product is filtered off (the filtrate is set aside) and dried, yielding 1 part of N-(2,3-dihydroimidazo[2,1-b]benzothiazol-8-yl)formamide; mp. 217° C.

The filtrate, which was set aside (see above), is evaporated. The residue is purified by column-chromatography over silica gel using a mixture of trichloromethane and methanol (95:5 by volume), saturated with ammonia, as eluent. The pure fractions are collected and the eluent is evaporated. The residue is converted into the hydrochloride salt in 2-propanol. The salt is filtered off and crystallized from 2-propanone, yielding 1.1 parts of 2,3-dihydro-N,N-dimethylimidazo[2,1-b]benzothiazol-8-amine dihydrochloride hemihydrate; mp. 205.9° C.

Example XXXI

A mixture of 7 parts of dimethyl carbonate, 3 parts of 2,3-dihydroimidazo[2,1-b]benzothiazol-6-amine and 70 parts of water is stirred and refluxed for 1 hour. The reaction mixture is cooled and alkalized with ammonium hydroxide. The precipitated product is filtered off and crystallized from ethanol, yielding 1.6 parts of N-(2,3-dihydroimidazo[2,1-b]benzothiazol-6-yl)acetamide; mp. 268° C.

Example XXXII

A mixture of 10 parts of 2,3-dihydro-7-methylimidazo[2,1-b]benzothiazol-6-amine and 120 parts of formic acid is stirred and refluxed for 3 hours. The reaction mixture is poured onto water and the whole is alkalized with ammonium hydroxide. The precipitated product is filtered off and crystallized from N,N-dimethylformamide, yielding, after drying, 6.3 parts of N-(2,3-dihydro-7-methylimidazo[2,1-b]benzothiazol-6-yl)formamide; mp. 256.8° C.

Example XXXIII

To a stirred mixture of 5.5 parts of N-(2,3-dihydro-7-methylimidazo[2,1-b]benzothiazol-6-yl)formamide and 80 parts of hexamethylphosphoric triamide are added portionwise 1.24 parts of sodium hydride dispersion 75.8%. After stirring for 2 hours at room temperature, there are added dropwise 4.9 parts of dimethyl sulfate. Upon completion, stirring is continued for 3 hours at 50° C. and overnight at room temperature. 4-Methyl-2-pentanone and water are added and the layers are separated. The aqueous phase is extracted twice with 4-methyl-2-pentanone. The combined organic phases are washed with water, dried, filtered and evaporated. The residue is crystallized from methylbenzene. The product is filtered off and dried, yielding 1.5 parts of N-(2,3-dihydro-7-methylimidazo[2,1-b]benzothiazol-6-yl)-N-methylformamide; mp. 164.2° C.

Example XXXIV

A stirred and warm solution of 4.5 parts of N-ethyl-2,3-dihydroimidazo[2,1-b]benzothiazol-6-amine in 30 parts of acetic acid is acidified with 2-propanol, saturated with gaseous hydrogen chloride. After cooling to room temperature, the formed hydrochloride salt is filtered off and dried at 150° C., yielding 2.1 parts of N-ethyl-2,3-dihydroimidazo[2,1-b]benzothiazol-6-amine monohydrochloride; mp. 289.2° C.

Example XXXV

A mixture of 3 parts of 2,3-dihydroimidazo[2,1-b]benzothiazol-7-amine, 15 parts of 2-bromo-2-methylpropane and 13.5 parts of N,N-dimethylformamide is stirred for 20 hours at 80° C. The reaction mixture is poured onto 50 parts of water. The precipitated product is filtered off, washed successively with water, 2-propanol and 2,2'-oxybispropane, and dried, yielding 3 parts of N-(2,3-dihydroimidazo[2,1-b]benzothiazol-7-yl)formamide monohydrobromide; mp. 287.3° C.

Example XXXVI

To a stirred mixture of 3 parts of imidazo[2,1-b]benzothiazol-6-amine, 16 parts of acetic acid and 32 parts of water is added dropwise a solution of 1.54 parts of potassium cyanate in 32 parts of water (slightly exothermic reaction). Upon completion, stirring is continued overnight at room temperature. The reaction mixture is alkalized with ammonium hydroxide. Upon stirring, the product is precipitated. It is filtered off and dried, yielding 3 parts of N-(2,3-dihydroimidazo[2,1-b]benzothiazol-6-yl)urea; mp. +300° C.

Example XXXVII

To a stirred mixture of 4 parts of (2,3-dihydroimidazo[2,1-b]benzothiazol-6-yl)phenylmethanone monohydrochloride, 3 parts of sodium methoxide and 60 parts of methanol are added portionwise 1.5 parts of sodium borohydride. Upon completion, stirring is continued for 5 minutes at reflux temperature. The reaction mixture is cooled and upon the addition of water, the product is allowed to crystallize. It is filtered off and recrystallized from 4-methyl-2-pentanone. The product is filtered off and dried, yielding 0.4 parts of 2,3-dihydro-$\alpha$-phenylimidazo[2,1-b]benzothiazole-6-methanol; mp. 175.2° C.

Example XXXVIII

A mixture of 10 parts of 7-ethoxy-2,3-dihydroimidazo[2,1-b]benzothiazole and 150 parts of hydrobromic acid solution 48% in glacial acetic acid is stirred and refluxed overnight. The reaction mixture is evaporated. The solid residue is washed with ethanol and crystallized from ethanol 80%. The product is filtered off and dried, yielding 8 parts of 2,3-dihydroimidazo[2,1-b]benzothiazol-7-ol monohydrobromide; mp. 259.9° C.

Example XXXIX

A mixture of 3.8 parts of 2,3-dihydro-7-methylimidazo[2,1-b]benzothiazole, 11 parts of (2-bromoethyl)benzene and 40 parts of acetonitrile is stirred and refluxed for 8 hours. After cooling, the precipitated product is filtered off and dried, yielding 6 parts of 2,3-dihydro-7-methyl-1-(2-phenylethyl)imidazo[2,1-b]benzothiazolium bromide; mp. 150.6° C.

In a similar manner there are also prepared:

7-butyl-1-hexyl-2,3-dihydroimidazo[2,1-b]benzothiazolium bromide; mp. 178.7° C.;

2,3-dihydro-7-methyl-1-(2-propynyl)imidazo[2,1-b]benzothiazolium bromide; mp. 242.5° C.;

6-amino-7-butyl-1-(2,6-dichlorophenylmethyl)-2,3-dihydroimidazo[2,1-b]benzothiazolium chloride monohydrate; mp. 152° C.;

2,3-dihydro-1-(1-methylethyl)-6-(propylamino)imidazo[2,1-b]benzothiazolium bromide; mp. 237.7° C.;

1-(2,6-dichlorophenylmethyl)-6-(ethylamino)-2,3-dihydroimidazo[2,1-b]benzothiazolium monochloride; mp. 268.3° C.; and 6-(ethylamino)-2,3-dihydro-1-methylimidazo[2,1-b]benzothiazolium monoiodide; mp. 273.8° C.

Example XL

To a stirred mixture of 10 parts of diethyl 2-[(2,3-dihydroimidazo[2,1-b]benzothiazol-7-ylamino)methylene]propanedioate, 1.1 parts of sodium hydride dispersion 76.8% and 100 parts of hexamethylphosphoric triamide are added 13.2 parts of 1-bromohexane. The whole is stirred over weekend at 50° C. The reaction mixture is poured onto methylbenzene. The latter is washed three times with water, dried, filtered and evaporated. The residue solidifies on triturating in 1,1'-oxybisethane. The product is filtered off and crystallized from 4-methyl-2-pentanone, yielding 4.5 parts of 7-{[2,2-bis(ethoxycarbonyl)ethenyl]hexylamino}-1-hexyl-2,3-dihydroimidazo[2,1-b]benzothiazolium bromide; mp. 162° C.

Example XLI

To a stirred solution of 0.5 parts of 2,3-dihydro-N-(1-methylethyl)imidazo[2,1-b]benzothiazol-8-amine in 16 parts of methanol is added a solution of 0.184 parts of copper dichloride dihydrate in 4 parts of methanol. The precipitated product is filtered off, boiled in 40 parts of methanol, filtered off again and dried in vacuo at room temperature. The product is further dried for 2 hours in vacuo at 120° C., yielding 0.47 parts of bis[2,3-dihydro-N-(1-methylethyl)imidazo[2,1-b]benzothiazol-8-amine] copper (2+) dichloride; mp. 207.9° C.

What is claimed is:

1. A composition to treat depressions, comprising an inert carrier and, as an active ingredient, an amount, which is effective to treat depressions, of a compound selected from the group consisting of a 2,3-dihydroimidazo[2,1-b]benzothiazole which may structurally be represented by the formula

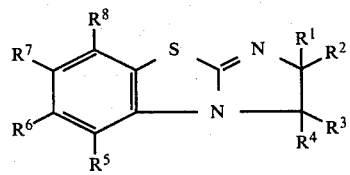

and the pharmaceutically acceptable acid addition salts thereof, the imidazo[2,1-b]benzothiazolium salts of formula

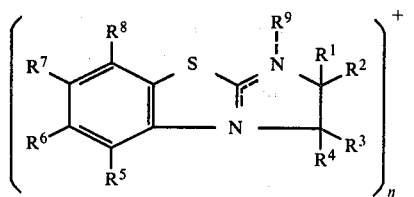

and metal salt complexes thereof with a transition metal salt, wherein:

$R^1$ and $R^3$ are each independently selected from the group consisting of hydrogen and lower alkyl;

$R^2$ and $R^4$ are each independently selected from the group consisting of hydrogen, lower alkyl, aryl, aryllower alkyl, lower alkyloxy-lower alkyl or aryloxylower alkyl;

$R^5$, $R^6$, $R^7$ and $R^8$ are each independently selected from the group consisting of hydrogen; halo; nitro; alkyl having from 1 to 20 carbon atoms; cycloalkyl having from 3 to 6 carbon atoms; hydroxy; lower alkyloxy; aryloxy; α-hydroxy-arylmethyl; amino; mono- and dialkyl-amino; mono-, di- and trihalo-lower alkylamino; lower alkenylamino; lower alkynylamino; (aryl-lower alkyl)amino; (lower alkyloxy-lower alkyl)amino; (hydroxy-lower alkyl)amino; (aryloxy-lower alkyl)amino; [mono- and di(lower-alkyl)amino-lower alkyl]amino; lower alkanoylamino; N-(lower alkyl)lower alkanoylamino; aminocarbonylamino; (1-lower alkyl-4-piperidinyl)amino; cycloalkylamino wherein said cycloalkyl represents a mono-, bi-, tri- or tetracyclic hydrocarbon radical having from 3 to 10 carbon atoms; and a radical of the formula

wherein $R^{10}$ is selected from the group consisting of hydrogen, lower alkyl, lower alkenyl and lower alkynyl; or, when taken together $R^5$ and $R^6$, $R^6$ and $R^7$, or $R^7$ and $R^8$ may form a tri- or tetramethylene bridge or complete a fused benzene nucleus;

$R^9$ is a member selected from the group consisting of lower alkyl, lower alkenyl, lower alkynyl and aryl lower alkyl; and X is a pharmaceutically acceptable anion and n represents the valency of the anion;

wherein aryl as used in the foregoing definitions is phenyl, optionally substituted with 1 to 3 substituents each independently selected from the group consisting of halo, lower alkyl, lower alkyloxy and trifluoromethyl; and aroyl is arylcarbonyl.

2. A composition to treat depressions, comprising an inert carrier and, as an active ingredient, an amount, which is effective to treat depressions, of a compound selected from the group consisting of N-ethyl-2,3-dihydroimidazo[2,1-b]benzothiazol-6-amine, the pharmaceutically acceptable acid addition salts thereof, are pharmaceutically acceptable corresponding imidazo[2,1-b]benzothiazolium salts thereof, and the metal salt complexes thereof with a transition metal salt.

3. A method of treating depressions in patients, which comprises the systemic administration to said patients, in need of same, of an effective anti-depressive amount of a compound selected from the group consisting of a 2,3-dihydroimidazo[2,1-b]benzothiazole which may structurally be represented by the formula

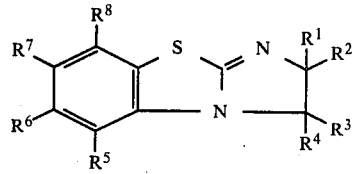

and the pharmaceutically acceptable acid addition salts thereof, and imidazo[2,1-b]benzothiazolium salts of formula

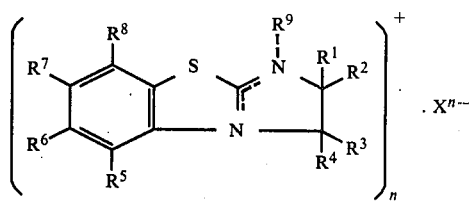

and metal salt complexes thereof with a transition metal salt, wherein:

$R^1$ and $R^3$ are each independently selected from the group consisting of hydrogen and lower alkyl;

$R^2$ and $R^4$ are each independently selected from the group consisting of hydrogen, lower alkyl, aryl, aryl-lower alkyl, lower alkyloxy-lower alkyl or aryloxy-lower alkyl;

$R^5$, $R^6$, $R^7$ and $R^8$ are each independently selected from the group consisting of hydrogen; halo; nitro; alkyl having from 1 to 20 carbon atoms; cycloalkyl having from 3 to 6 carbon atoms; hydroxy; lower alkyloxy; aryloxy; α-hydroxy-arylmethyl; amino; mono- and dialkyl-amino; mono-, di- and trihalo-lower alkylamino; lower alkenylamino; lower alkynylamino; (aryl-lower alkyl)amino; (lower alkyloxy-lower alkyl)amino; (hydroxy-lower alkyl)amino; (aryloxy-lower alkyl)amino; [mono- and di(lower alkyl)amino-lower alkyl]amino; lower alkanoylamino; N-(lower alkyl)lower alkanoylamino; aminocarbonylamino; (1-lower alkyl-4-piperidinyl)amino; cycloalkylamino wherein said cycloalkyl represents a mono-, bi-, tri- or tetracyclic hydrocarbon radical having from 3 to 10 carbon atoms; and a radical of the formula

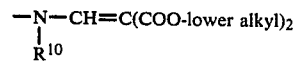

wherein $R^{10}$ is selected from the group consisting of hydrogen, lower alkyl, lower alkenyl and lower alkynyl; or, when taken together $R^5$ and $R^6$, $R^6$ and $R^7$, or $R^7$ and $R^8$ may form a tri- or tetramethylene bridge or complete a fused benzene nucleus;

$R^9$ is a member selected from the group consisting of lower alkyl, lower alkenyl, lower alkynyl and aryl-lower alkyl; and X is a pharmaceutically acceptable anion and n represents the valency of the anion;

wherein aryl as used in the foregoing definitions is phenyl, optionally substituted with 1 to 3 substituents each independently selected from the group consisting of halo, lower alkyl, lower alkyloxy and trifluoromethyl; and aroyl is arylcarbonyl.

* * * * *

UNITED STATES PATENT AND TRADEMARK OFFICE
CERTIFICATE OF CORRECTION

PATENT NO. : 4,262,004
DATED : April 14, 1981
INVENTOR(S) : Victor Sipido

It is certified that error appears in the above—identified patent and that said Letters Patent is hereby corrected as shown below:

Claim 2, Column 31, line 61: change "are" to --the--.

Signed and Sealed this

Third Day of November 1981

[SEAL]

Attest:

GERALD J. MOSSINGHOFF

Attesting Officer

Commissioner of Patents and Trademarks